US00PP21853P2

(12) United States Plant Patent
Ui et al.

(10) Patent No.: US PP21,853 P2
(45) Date of Patent: Apr. 5, 2011

(54) ***PETUNIA-CALIBRACHOA* PLANT NAMED 'SAKPXC007'**

(50) Latin Name: ***Petunia-Calibrachoa* Hybrid**
Varietal Denomination: SAKPXC007

(75) Inventors: Akinobu Ui, Iwata (JP); Shin Ishikawa, Shizuoka (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/655,960

(22) Filed: Jan. 11, 2010

(51) Int. Cl.
*A01H 5/00* (2006.01)

(52) U.S. Cl. ..... Plt./356

(58) Field of Classification Search ..... Plt./356
See application file for complete search history.

*Primary Examiner* — Annette H Para

(74) *Attorney, Agent, or Firm* — Jondle & Associates, P.C.

(57) ABSTRACT

'SAKPXC007' is a new *Petunia-Calibrachoa* intergeneric hybrid particularly distinguished by having a rosy-red flower color, good blooming ability, and mounding plant growth habit.

1 Drawing Sheet

Genus and species: *Petunia-Calibrachoa* Hybrid.
Variety denomination: 'SAKPXC007'.

BACKGROUND OF THE INVENTION

The present invention comprises a new and distinct cultivar of *Petunia-Calibrachoa* referred to by the variety name 'SAKPXC007'. 'SAKPXC007' originated from a hybridization in Kakegawa, Japan in October 2005. The male parent was a proprietary hybrid *Calibrachoa* line named '05-25' (unpatented), which had a scarlet flower color, small flower size, and a creeping plant growth habit. The female parent was a proprietary hybrid *Petunia* line named 'AM5-264' (unpatented), which had a rose flower color, medium flower size, and a mounding plant growth habit.

In October 2005, the new *Petunia-Calibrachoa* variety was developed using an intergeneric cross between *Petunia hybrida* and a *Calibrachoa hybrida* species. After crossing the parent lines, 650 ovules were removed from flowers on the female parent and cultured by standard ovule culture techniques. In March 2006, ten intergeneric hybrid plantlets were transplanted to soil-less media for greenhouse culture and acclimatization.

In June 2006, ten plants out of ten hybrid lines were vegetatively propagated to produce rooted cuttings. In July 2006, the ten plants were transplanted to an open field and evaluated for flower color and plant growth habit through November. In December 2006, one plant which had a rosy-red flower color, good blooming ability, and a mounding plant habit was selected and vegetatively propagated. In March 2007, ten cuttings were evaluated in an open field through June 2007. In June 2007, it was confirmed that the distinct characteristics of the selection were fixed and stable. The selection was named 'SAKPXC007'. All breeding work was conducted at Kakegawa Research station in Kakegawa Japan.

'SAKPXC007' has been found to reproduce true to type in successive generations of asexual propagation via vegetative cuttings.

SUMMARY OF THE INVENTION

The following are the most outstanding and distinguishing characteristics of this new variety when grown under normal horticultural practices in Kakegawa, Japan.

1. Rosy-red flower color;
2. Good blooming ability; and
3. A mounding plant growth habit.

DESCRIPTION OF THE PHOTOGRAPHS

This new *Petunia-Calibrachoa* plant is illustrated by the accompanying photographs which show the plant's form, foliage, and flowers.

The photographs are of a plant four months old grown in Salinas, Calif. in Summer/Fall 2009. The colors shown are as true as can be reasonably obtained by conventional photographic procedures.

DESCRIPTION OF THE NEW VARIETY

Figure 1:
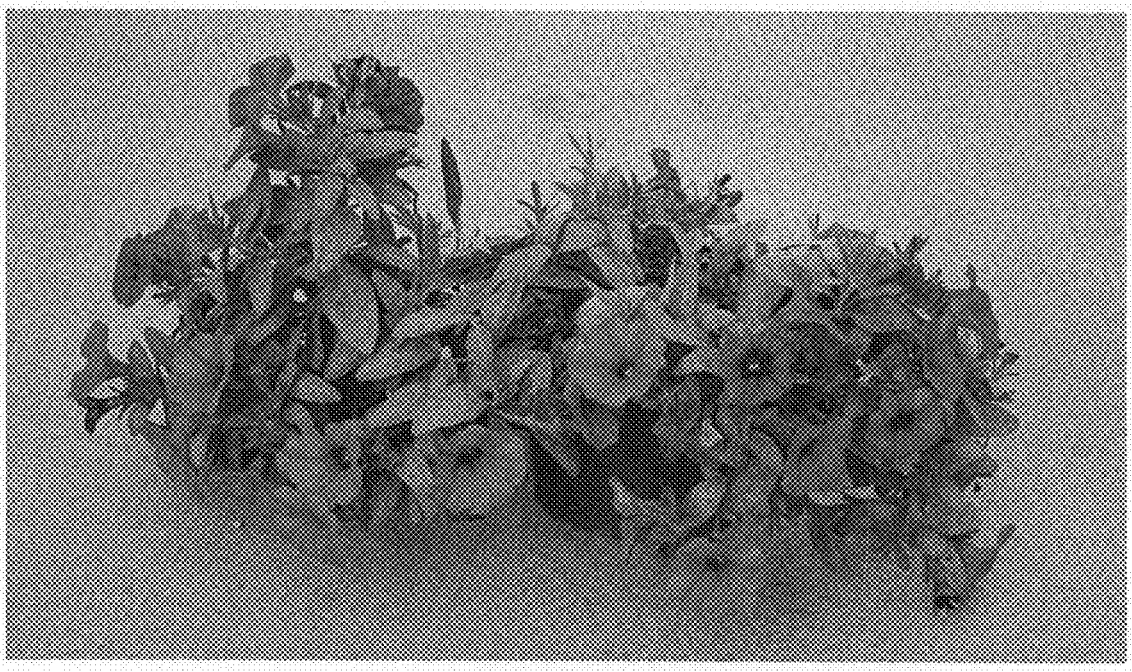
FIG. 1 shows the overall plant habit.
Figure 2:
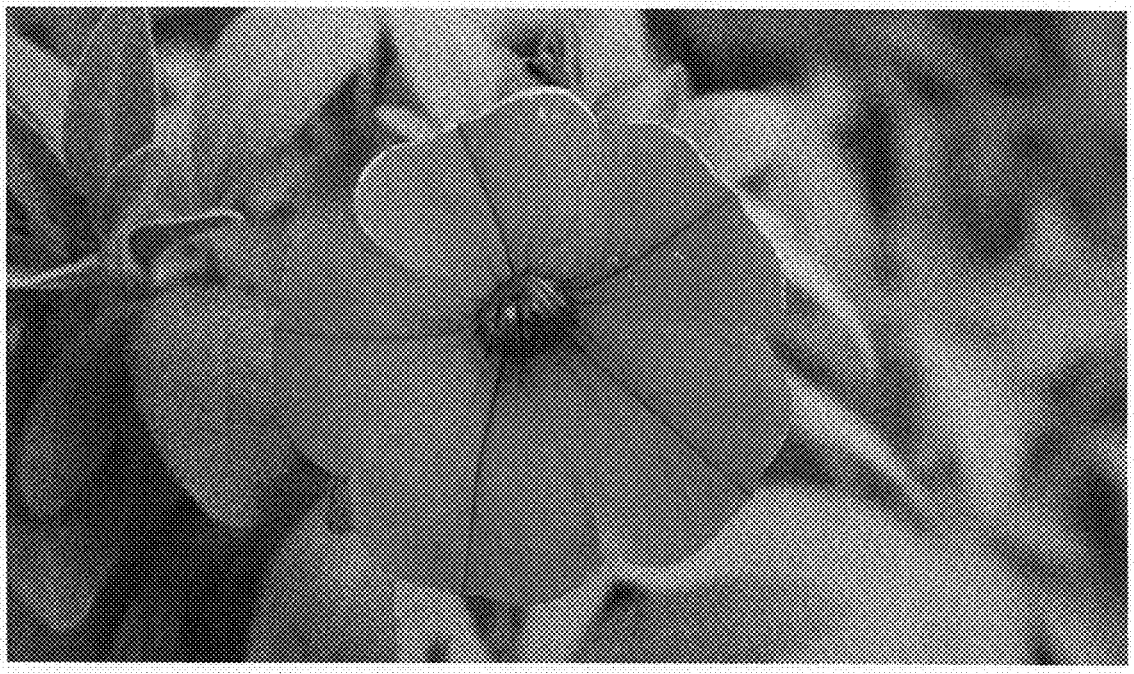
FIG. 2 shows a close-up of the mature flower.

The following detailed description sets forth the distinctive characteristics of 'SAKPXC007'. The data which define these characteristics were collected from asexual reproductions carried out in Salinas, Calif. in 2009. The detailed description was taken from plants grown under greenhouse conditions for approximately four months from transplanting of rooted cuttings. Color references are to The R.H.S. Colour Chart of The Royal Horticultural Society of London (R.H.S.), 4$^{th}$ Edition.

DETAILED BOTANICAL DESCRIPTION

Classification:
- *Family.*—Solanaceae.
- *Botanical.*—*Petunia-Calibrachoa* intergeneric hybrid.
- *Common name.*—Petchoa.
- *Variety name.*—'SAKPXC007'.

Parentage:
- *Male.*—Proprietary hybrid *Calibrachoa* plant '05-25' (unpatented).
- *Female.*—Proprietary hybrid *Petunia* plant 'AM5-264' (unpatented).

Plant description:
- *Life cycle.*—Tender perennial.

*Form.*—Decumbent, branching.
*Habit.*—Mounding.
*Height.*—14.0 cm to 15.0 cm (from soil line to top of foliage).
*Spread.*—43.0 cm to 44.0 cm.

Propagation:
*Type cuttings.*—Vegetative cuttings.
*Time to produce a rooted cutting.*—4 weeks.
*Time to bloom from propagation.*—8 to 10 weeks.

Environmental conditions for plant growth: The terminal 1.0 to 1.5 inches of an actively growing stem was excised. The vegetative cuttings were propagated in four weeks. The base of the cuttings were dipped for one to two seconds in a 1:9 solution (1 solution: 9 water) of DIP 'N GROW root inducing solution immediately prior to sticking into the cell trays. Cuttings were stuck into plastic cell trays having 98 cells, and containing a moistened peat moss-based growing medium. For the first week, the cuttings were misted with water from overhead for 20 seconds, one time per hour. For the second week, the cuttings were misted one time every two hours for 10 seconds. After that time, the cuttings were misted occasionally until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus, and 18% potassium. The typical average air temperature was 24° C.

Stems:
*Stem color.*—RHS 144B (Yellow-green).
*Anthocyanin color.*—Slightly present on stems, RHS N77A (Purple).
*Pubescence.*—Heavy, RHS N155A (White).
*Stem description.*—Circular, cross-section.
*Stem diameter.*—0.2 cm to 0.3 cm.
*Stem length.*—4.0 cm from soil line to first node, 12.0 cm to 13.0 cm total length.
*Internode length.*—2.0 cm.

Leaves:
*Arrangement.*—Alternate.
*Shape.*—Elliptical.
*Apex.*—Obtuse.
*Base.*—Attenuate.
*Margin.*—Entire.
*Surface appearance.*—Dull.
*Surface pubescence.*—Light, RHS N155A (White).
*Length.*—5.0 cm.
*Width.*—2.0 cm.
*Color.*—Upper surface: RHS 137A (Green). Lower surface: RHS 137B (Green).
*Fragrance.*—Absent.
*Venation.*—Pinnate.
*Venation color.*—Upper surface: RHS 137B (Green). Lower surface: RHS 137C (Green).

Flower buds:
*Surface.*—Pubescent.
*Length.*—3.0 cm.
*Diameter.*—1.0 cm.
*Shape.*—Ovate.
*Color.*—RHS 79A (Purple).

Flowers (inflorescence):
*Total number of flowers per plant.*—35.
*Flowering habit.*—Indeterminate.
*Flower type.*—Solitary.
*Flowering requirements.*—Will flower so long as day length is greater than 12 hours and temperature exceeds 13° C.
*Lastingness of flowers on the plant.*—5 days.
*Corolla.*—Composed of 5 petals, fused at the base, the flowers are funnel shaped with five fissures and a shallow, yet slight, indentation of the petal tip at the midvein.
*Corolla diameter.*—5.0 cm.
*Fragrance.*—Absent.
*Flower depth.*—1.0 cm.
*Flower diameter.*—5.0 cm.
*Flower tube length.*—2.5 cm.
*Flower tube diameter.*—1.0 cm.
*Petal.*—Apex: Truncate. Base: Fused. Margin: Entire. Texture: Glabrous. Length: 2.0 cm. Width: 2.5 cm. Petal (lobe) color: Upper surface: Closest to RHS 61B (Red-purple). Lower surface: RHS 59D (Red-purple) with RHS N77A (Purple) veins.
*Corolla tube color.*—Inner: RHS 13A (Yellow) with RHS N77A (Purple) veins. Outer: RHS 1D (Green-yellow) with N77A (Purple) veins.
*Calyx.*—Composed of 5 sepals, fused below the middle.
*Sepals.*—Shape: Elliptical. Apex: Obtuse. Margin: Entire. Length: 2.5 cm. Diameter: 0.4 cm. Color (both surfaces): RHS 137C (Green).
*Peduncle.*—Length: 1.0 cm. Diameter: 0.10 cm. Color: RHS 144B (Yellow-green) with RHS N77A (Purple) anthocyanin. Texture: Dull, slightly pubescent.

Reproductive organs:
*Stamen number.*—5 and free.
*Stamen.*—Anther color: RHS 10A (Yellow). Filament color: RHS 2C (Yellow). Pollen color: RHS 10B (Yellow).
*Ovary.*—Superior.
*Placenta arrangement.*—Central.
*Pistil number.*—1 per inflorescence.
*Pistil length.*—1.5 cm.
*Stigma color.*—RHS 145C (Yellow-green).
*Style length.*—1.4 cm.
*Style color.*—RHS 145C (Yellow-green).

Fruit/seed set: No fruit or seeds produced.

Disease and insect resistance: 'SAKPXC007' has excellent resistance to rain, heat, and drought. A temperature below 10° C. is not optimal. Plants are susceptible to *Botrytis,* powdery mildew, various stem and root rots, and certain viruses, like Tobacco Mosaic Virus and Impatiens Necrotic Spotted Virus. Plants can be infested with aphids, leafminer, whitefly, and various *Lepitopdera.*

COMPARISON WITH PARENTAL LINES AND KNOWN CULTIVAR

As shown in Table 1, 'SAKPXC007' is distinguished from its parents mainly by flower color and plant growth habit.

TABLE 1

| Characteristic | 'SAKPXC007' | Male Parent: '05-25' | Female Parent: 'AM5-264' |
|---|---|---|---|
| Flower color | Rosy-red | Rose | Scarlet |
| Plant growth habit | Mounding | Creeping | Mounding |

'SAKPXC007' is most similar to the commercial *Calibrachoa-Petunia* variety 'Kakegawa S89' (U.S. Plant Pat. No.

19,130), commercially known as SUPERCAL NEON ROSE. Differences in the flower color of 'SAKPXC007' when compared to 'Kakegawa S89' are shown in Table 2. Color references are to The R.H.S. Colour Chart of The Royal Horticultural Society of London (R.H.S.), 4$^{th}$ Edition.

TABLE 2

| Characteristic | 'SAKPXC007' | 'Kakegawa S89' |
|---|---|---|
| Petal color, upper surface | Closest to RHS 61B (Red-purple) | RHS N66A (Red-purple) with RHS 64A (Red-purple) veins |

TABLE 2-continued

| Characteristic | 'SAKPXC007' | 'Kakegawa S89' |
|---|---|---|
| Petal color, lower surface | RHS 59D (Red-purple) with RHS N77A (Purple) veins | RHS N66C (Red-purple) with RHS 142A (Green) veins |

I claim:

1. A new and distinct cultivar of *Petunia-Calibrachoa* hybrid plant as shown and described herein.

* * * * *